(12) United States Patent
Baker et al.

(10) Patent No.: US 9,895,058 B2
(45) Date of Patent: Feb. 20, 2018

(54) HEADS-UP VISION ANALYZER

(75) Inventors: Christopher Baker, Moraga, CA (US);
Tobias Buehren, Magdala (DE); James Foley, Fremont, CA (US)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 13/429,602

(22) Filed: Mar. 26, 2012

(65) Prior Publication Data

US 2012/0287398 A1    Nov. 15, 2012

Related U.S. Application Data

(60) Provisional application No. 61/467,486, filed on Mar. 25, 2011.

(51) Int. Cl.
*A61B 3/103* (2006.01)
*A61B 3/113* (2006.01)
*A61B 3/15* (2006.01)

(52) U.S. Cl.
CPC ............... *A61B 3/103* (2013.01); *A61B 3/113* (2013.01); *A61B 3/152* (2013.01)

(58) Field of Classification Search
CPC ......... A61B 3/10; A61B 3/103–3/1035; A61B 3/02; A61B 3/032; A61B 3/036; A61B 3/09
See application file for complete search history.

(56) References Cited

U.S. PATENT DOCUMENTS

| 5,949,521 | A | 9/1999 | Williams et al. |
| 5,963,300 | A | 10/1999 | Horwitz |
| 6,741,359 | B2 | 5/2004 | Wei et al. |
| 6,752,499 | B2 | 6/2004 | Aller |
| 6,761,454 | B2 * | 7/2004 | Lai et al. ............ 351/216 |
| 6,997,555 | B2 | 2/2006 | Dick et al. |

(Continued)

FOREIGN PATENT DOCUMENTS

WO    WO 2005000112 A1    1/2005

OTHER PUBLICATIONS

Technical Note: Calibration of the Canon Autoref R-1 for continuous measurement of accommodation, Brett Davis, Michael Collins, David Atchison; Ophthal. Physiol. Opt. 1993 vol. 13, pp. 191-198.

(Continued)

*Primary Examiner* — Ricky Mack
*Assistant Examiner* — Robert E Tallman
(74) *Attorney, Agent, or Firm* — Leydig, Voit & Mayer, Ltd.

(57) ABSTRACT

A binocular vision analyzer apparatus is used for determining a prescription of visual aids for the eyes of an individual. The apparatus includes first and second targets respectively corresponding to the first and second eyes of the individual and at least one illuminator unit for illuminating the targets. An optical system is configured to present respective virtual images of the first and second targets so as to be viewable by the respective first and second eyes. At least one beam splitter disposed in front of the first and second eyes directs the virtual images toward the respective eyes. The apparatus also includes first and second spherical correction devices and first and second cylindrical correction devices that respectively correspond to the first and second eyes.

29 Claims, 9 Drawing Sheets

(56) References Cited

U.S. PATENT DOCUMENTS

| | | |
|---|---|---|
| 7,077,522 B2 | 7/2006 | Williams |
| 7,225,442 B2 | 5/2007 | Dutta et al. |
| 7,357,509 B2 | 4/2008 | Williams et al. |
| 7,387,387 B2 | 6/2008 | Dai |
| 7,407,289 B2 * | 8/2008 | Sakurada ..................... 351/211 |
| 7,425,067 B2 * | 9/2008 | Warden ................ A61B 3/0075 |
| | | 351/205 |
| 7,559,652 B2 | 7/2009 | Lindacher |
| 7,673,992 B2 | 3/2010 | Wengler |
| 7,744,217 B2 | 6/2010 | Cabeza et al. |
| 2005/0105047 A1 | 5/2005 | Smitth, III et al. |
| 2008/0018855 A1 * | 1/2008 | Larichev et al. ............ 351/211 |
| 2009/0153796 A1 * | 6/2009 | Rabner ....................... 351/201 |

OTHER PUBLICATIONS

COAS-VRTM Wavefront Aberrometer Technical Description, AMO WaveFront Sciences LLC, Albuquerque, New Mexico, pp. 1-2.

COAS-VRTM Wavefront Aberrometer, AMO WaveFront Sciences LLC, Albuquerque, New Mexico, pp. 1-2.

\* cited by examiner

HEADS-UP VISION ANALYZER

CROSS REFERENCE TO RELATED APPLICATIONS

This application claims priority to U.S. Provisional Patent Application No. 61/467,486, filed Mar. 25, 2011, which is hereby incorporated by reference herein in its entirety.

FIELD

The present invention relates generally to vision analysis and in particular to a binocular vision analyzer apparatus and method for determining a prescription of visual aids.

BACKGROUND

State of the art determination of prescription for an individual generally includes a two step process. First a start value for each eye is captured objectively with an auto-refractor. Each eye is measured consecutively while the patient is fixating a target inside the device. The results are then transferred into a trial frame or phoropter head and refraction is fine-tuned based on subjective feedback from the patient in a second separate step. For a complete eye examination of visual performance, additional tests such as pupil distance, heterophoria, binocular balance or near-addition tests etc. are performed during subjective refraction. These tests enable the practitioner, with the subjective information from the patient, to select a visual aid (e.g. progressive spectacle lenses, simultaneous vision bifocal contact lenses, intraocular lenses, LASIK procedures etc.).

Several factors are responsible for the limited accuracy of auto-refractors determining prescription. A well known issue is instrument myopia caused by the close proximity of the device in front of the eye despite target projection into infinity by optical means. Lack of control of focus and vergence of the non-measured eye and other factors add to the instrument myopia problem. Some auto-refractors try to overcome these problems by providing open space natural binocular viewing conditions while measuring refraction of the eye. Although their results show better correlation they are still not always identical to subjective refraction. There are further significant reasons for this, for example the refraction found monocularly for each eye can change when the eyes are operating together (hence the requirement for binocular balance measurements) and there may be cyclo-rotation of the eyes which will affect cylinder angle. Additional but required tests to provide prism correction cannot be performed monocularly. There is also an element of patient acceptance when defining the correct prescription and subjective binocular refraction allows patients to express their preference. For these reasons subjective binocular refraction is considered the gold standard.

Wavefront sensors provide a more detailed objective picture of visual performance by measuring lower and higher order aberrations of the eye. Generally they encounter the same problems caused by unnatural viewing conditions during measurement as auto-refractors and similar measures to address them have been proposed. Recently introduced ocular aberration based techniques for prescribing visual aids appear to partially overcome the need for subjective refraction. Today, however, practitioners applying these new techniques still perform subjective refraction because sphere, cylinder and axis values, and the higher order corrections available with wavefront refraction, are not the only values that provide a complete prescription (see above).

Another typical step in the process that starts with visiting an eye doctor or optometrist and ends with wearing a satisfactory vision aid is the varying subjective tolerance of individuals to optical designs of vision aids, particularly to bifocal or multifocal designs. It is very difficult for the practitioner to predict how the patient's subjective tolerance to an optical design will be without actually putting the optical design in front of the patient's eyes. For example it is typically not advised to prescribe progressive lenses to someone who has worn bifocal lenses for many years: in such a case the likelihood is high that the patient will not get used to the progressive lens design, though the underlying reasons for this are not well understood. This issue becomes particularly critical when simultaneous vision intraocular lenses are implanted in a cataract surgery procedure. Not only is it not possible to put the design in front of the patient's eye before surgery, it is also not possible to remove the design easily post-surgery should the patient reject the visual performance of simultaneous vision. The possibility to get individual subjective tolerance feedback to an optical design before a visual aid is ordered and manufactured would be a significant asset for the practitioner's decision making process.

The relevance of individual subjective tolerance to optical designs will increase in the future. Therapeutic optical designs to control myopia are on the horizon. These new designs will fundamentally change the objective of optical prescriptions from pure symptom treatment methods to therapeutic prevention or curing methods of refractive errors. The two most important aspects of these procedures will be firstly the efficiency of the therapeutic treatment effect and secondly individual subjective tolerance to the therapeutic optical design. Again, the possibility to get individual subjective tolerance feedback to a therapeutic optical design before a visual aid is ordered and manufactured would be a substantial asset for the practitioner's decision making process.

U.S. Pat. No. 5,963,300 to Horwitz describes an ocular biometer for monocular and binocular interferometric wavefront and other measurement of the eye utilizing "hot mirrors" to allow the eye to view the world as the ocular biometer objectively measures various characteristics of the eye such as convergence via Purkinje images. Thus Horwitz, among others, enables strabismus measurements.

However, Horwitz fails to control and measure vergence by means of virtual images that can be optically separated for each eye and individually displaced either horizontally or vertically. Therefore no heterophoria measurements can be performed. Horwitz furthermore does not take into account subjective measurement procedures such as heterophoria, binocular balance, or subjective refraction feedback to be combined with objective measurements.

The major drawbacks of other measurement techniques for the determination of visual aids of the human eye are the unnatural viewing condition used by objective measurement methods (subsequent monocular measurement of each eye combined with instrument myopia) as well as the separation of objective and subjective measurement techniques into two work steps. While there are several objective measurement techniques that use open space viewing conditions (e.g. Canon, Wavefront Sciences) it is not possible to get subjective visual feedback from the patient to optimize or modify the result of these devices in any form and it is not possible to control vergence. Neither is it possible to simulate visual perception of visual correction methods for example induced by multi-focal contact lenses or spectacles.

Adaptive optics systems to measure and correct all aberrations of the eye have been described in various implementations, that can include an incorporated eye tracking system, binocular measurement, far and near distance measurement and photopic or mesopic viewing conditions. However none of these systems take into account the natural viewing conditions of the eye under binocular free space viewing that is required to fine tune both objective and subjective individual vision corrections.

SUMMARY

In an embodiment, the present invention provides a binocular vision analyzer apparatus for determining a prescription of visual aids for the eyes of an individual. The apparatus includes first and second targets respectively corresponding to the first and second eyes of the individual and at least one illuminator unit for illuminating the targets. An optical system is configured to present respective virtual images of the first and second targets so as to be viewable by the respective first and second eyes. At least one beam splitter disposed in front of the first and second eyes directs the virtual images toward the respective eyes. The apparatus also includes first and second spherical correction devices and first and second cylindrical correction devices that respectively correspond to the first and second eyes.

BRIEF DESCRIPTION OF THE DRAWINGS

Exemplary embodiments of the present invention are described in more detail below with reference to the drawings, in which.

DETAILED DESCRIPTION

In one embodiment of the present invention, diagnosis, treatment and therapy planning of vision correction techniques for the human eye can be improved by combining objective and subjective refraction techniques. This can be achieved by the use of virtual heads-up displays of targets for each eye separately, an optometer unit, a wavefront sensor unit and an adaptive optics unit. Virtual heads-up displays of targets serve to control binocular vergence and to avoid instrument myopia. Virtual targets can be modified by objectively measuring optical aberrations using an optometer unit and a wavefront sensor unit. Such aberrations can be compensated for by use of conventional techniques such as a Badal optometer and Stokes cell or the adaptive optics unit or combinations thereof and projected via virtual heads-up displays of targets into each eye. Within an interactive process between operator and patient, the optically compensated or modified aberrations can be subjectively refined by assessment of monocular and binocular vision as well as heterophoria measurements using known subjective refraction test procedures.

Aberrations are measured objectively and corrected or modified under monocular and binocular viewing conditions, for far and near distance viewing, having the ability to get feedback on the automatic correction of these objective measurements from the patient in an interactive process between operator and patient. Thereby, factors such as monocular versus binocular vision, photopic versus mesopic vision (i.e. vision that varies with pupil size), vergence and subjective visual perception under dynamic viewing conditions can be assessed.

Using adaptive optics technology, the invention furthermore provides the ability to simulate optical performance of vision correction methods (e.g. spectacles, contact lenses or intraocular lenses) of various designs such as monofocal lenses, progressive lenses, or simultaneous vision multifocal lens designs, by projecting corresponding virtual images into the eyes. The ability to simulate optical performance of future therapeutic optical designs to control myopia will also be possible. Thereby, appropriate dimensions of virtual image projections will allow simulating not only central but also peripheral vision. The possibility to get individual subjective tolerance feedback to a conventional or therapeutic optical design before a visual aid is ordered and manufactured will be a substantial asset for the practitioner's decision making process.

Figure 1:
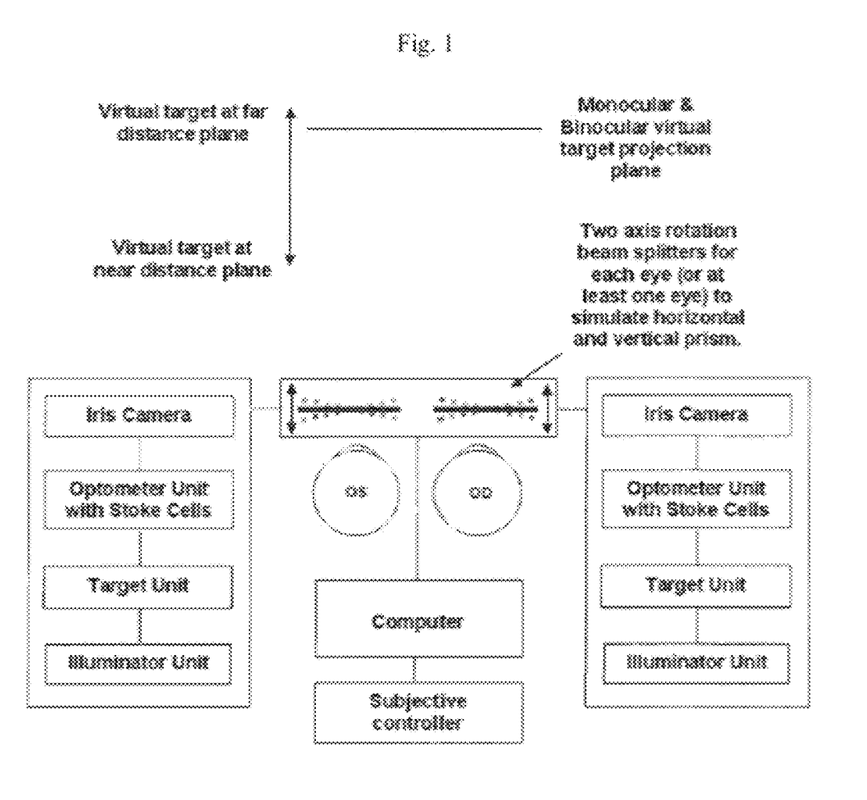
FIG. 1 schematically depicts an embodiment of a binocular vision analyzer apparatus.
Figure 2:
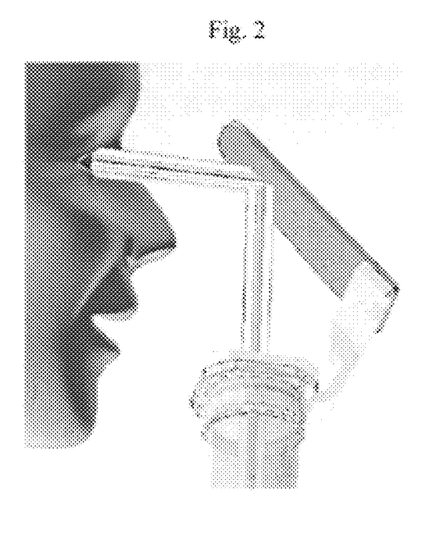
FIG. 2 shows a beam splitter for presenting a virtual target image to an individual's eye.

An embodiment of the present invention is schematically depicted in FIG. 1 and includes an adjustable binocular heads-up display of two virtual targets, a spherical correction device (e.g. a Badal Optometer) and a cylindrical correction device (e.g. Stokes cells), a target unit, an illuminator unit and an iris camera. The binocular heads-up display uses two separate and individually adjustable beam splitters, one for each eye, for horizontal and vertical vergence control. The projection of the virtual image to the eye of the patient by one of the adjustable beam splitters is shown in FIG. 2.

The binocular heads-up refractor apparatus depicted in FIG. 1 can include the following advantageous features:
a. A tabletop design;
b. Adjustable binocular heads-up display of two virtual targets, allowing for control of vergence;
c. Open space monocular and binocular subjective refraction measurement;
d. Heterophoria, fusional reserve and stereopsis measurement;
e. Binocular balance measurement; and
f. Interface for auto-refraction data import as start values for subjective refraction procedure.

The operation of the binocular heads-up refractor apparatus can be controlled using a computing device, or computer as shown in FIG. 1. The computing device can be a stand-alone personal computer that is coupled to the apparatus, or it can be a printed circuit board, processor or one or more microprocessors integrated into the apparatus. The computing device can be used for electrical actuation of the individual components of the binocular heads-up refractor, for example, through the use of switches or motors. The computing device can also be used to determine certain aspects of the individual's prescription such as spherical correction provided by the spherical correction device, cylindrical correction provided by the cylindrical correction device, or measurements determined based on adjustment of the apparatus for aligning with the individual's eyes. The computing device can also include or be in communication with a memory for storing settings and measurements of the binocular refractor apparatus. The memory is preferably a tangible non-transitory computer readable media, such as ROM, RAM or EEPROM.

Figure 3:
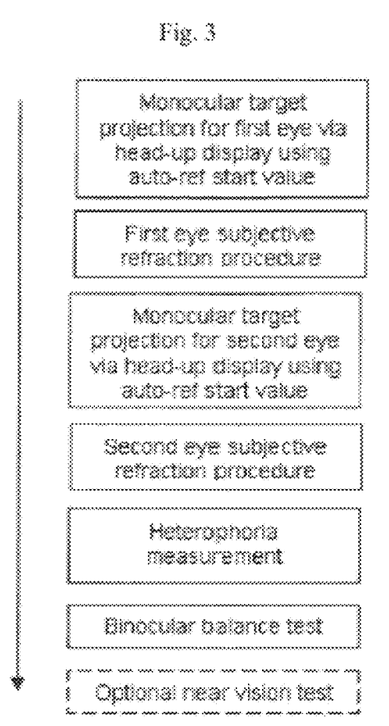
FIG. 3 shows a flow diagram of a method of using the analyzer apparatus of FIG. 1.

FIG. 3 shows various steps that can be carried out when using the apparatus depicted in FIG. 1. As start values for monocular target projection into the first eye, refraction values (RX) can be set manually or imported via a data interface for RX data.

In a next step the subjective refraction procedure is performed using the optometer unit and Stokes cells in a similar interactive process between operator and patient as known from traditional subjective refraction procedures albeit without physically positioning lenses in front of the patients' eyes but by modification of virtual target projection. Following monocular refraction of the first eye the same process is repeated for the second eye.

Heterophoria measurement can be achieved by projection of state of the art heterophoria measurement tests (e.g. fixation disparity test) and via horizontal and/or vertical adjustment of beam splitters of the heads-up displays. The heterophoria measurement procedure will be performed in a similar interactive process between operator and patient as known from traditional heterophoria measurement procedures albeit not by means of prisms lenses in front of the patients' eyes but via adjustment of the heads-up display.

In a last step, binocular balance testing can be achieved by binocular projection of targets for both eyes via heads-up displays. The binocular balance testing procedure can be performed in a similar interactive process between operator and patient as known from traditional binocular balance tests (e.g. red green test) albeit without the use of optical separators such as polarizing filters or red/green filters, but by individual monocular target projection under binocular target viewing conditions.

In an optional step, near vision testing can be performed by projection of virtual targets at various distances in front of the eye. The near vision testing procedure will be performed in a similar interactive process between operator and patient as known from traditional near vision tests albeit without the use of near addition lenses and real targets at close proximity to the eye but by projection of virtual targets that are focused and converged at various distances in front of the eye by means of the refraction correction and prism simulation mechanisms previously described.

Figure 4:
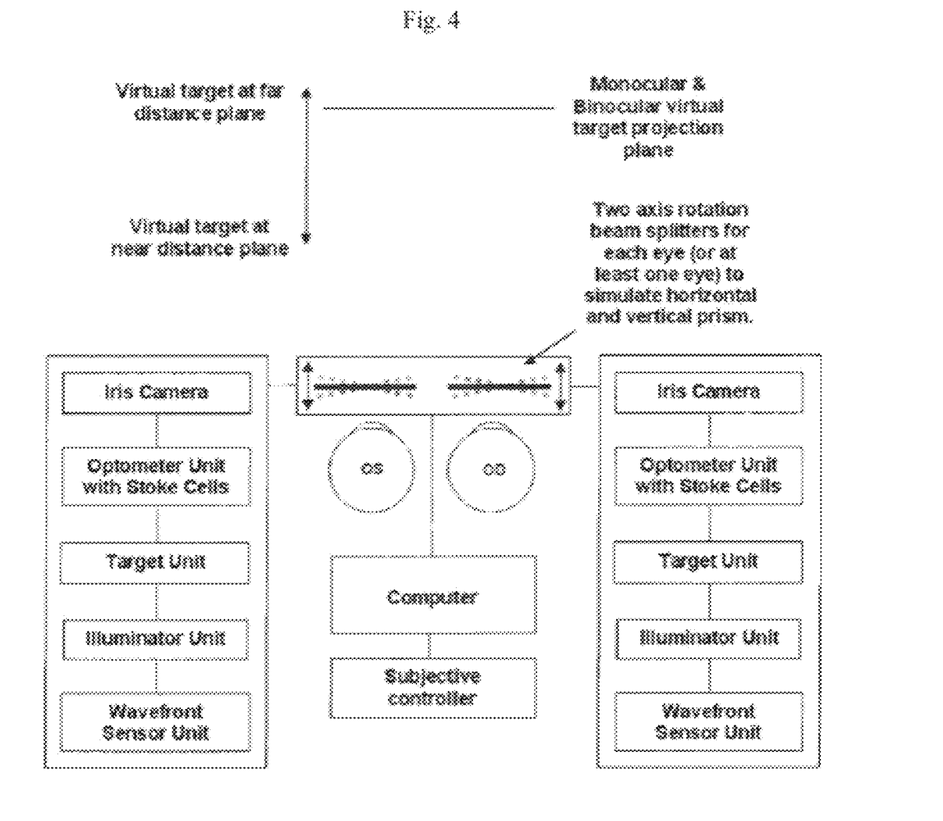
FIG. 4 schematically depicts another embodiment of a binocular vision analyzer apparatus.

II. FIG. 4 shows a table top design binocular heads-up refractor apparatus in accordance with an embodiment of the present invention that includes a wavefront sensor unit. The apparatus includes an adjustable binocular heads-up display of two virtual targets, a spherical correction device (e.g. a Badal Optometer) and a cylindrical correction device (e.g. Stokes cells}, a target unit, an illuminator unit, an iris camera and the wavefront sensor unit.

Two-axis rotation beam splitters for each eye (or at least one eye) can be used to simulate horizontal and vertical prism.

The binocular heads-up refractor apparatus for combined objective and subjective refraction depicted in FIG. 4 can include the following advantageous features:
a. A tabletop design;
b. Adjustable binocular heads-up display of two virtual targets, for control of vergence;
c. Ocular lower and higher-order aberration measurement;
d. The ability to automatically modify virtual, heads-up display of targets by compensating lower order aberrations of the eye with the optometer as a start value for subjective refraction;
e. Open space monocular and binocular subjective refraction measurement;
f. Heterophoria measurement;
g. Binocular balance measurement; and
h. The ability to employ retinal image based refraction techniques under binocular open space viewing conditions.

Figure 5:
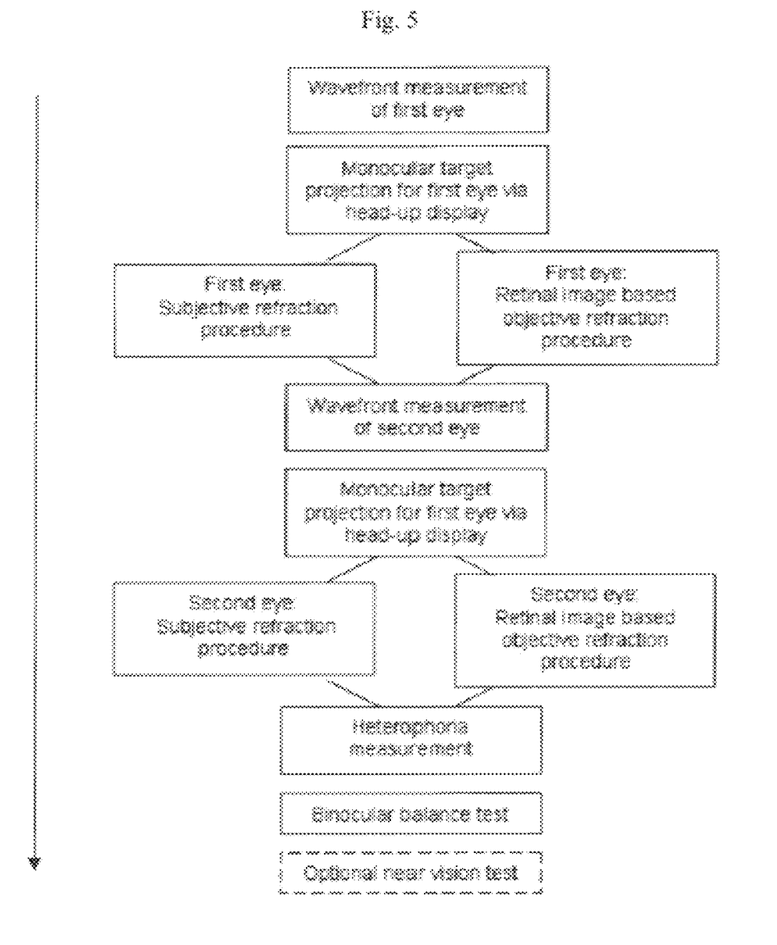
FIG. 5 shows a flow diagram of a method of using the analyzer apparatus of FIG. 4.

FIG. 5 shows various steps that can be carried out when using the apparatus depicted in FIG. 4. For the first eye, wavefront aberrations are measured objectively and lower order aberrations are compensated for via the optometer unit with Stokes cells.

In a next step the subjective refraction procedure is performed using the optometer unit with Stokes cells in a similar interactive process between operator and patient as known from traditional subjective refraction procedures albeit without physically positioning lenses in front of the patients' eyes but by modification of virtual target projection into the eye. Following monocular refraction of the first eye, the same process is repeated for the second eye.

Heterophoria measurement can be achieved by projection of state of the art heterophoria measurement tests (e.g. fixation disparity test) and via horizontal and/or vertical adjustment of the heads-up displays. The heterophoria measurement procedure will be performed in a similar interactive process between operator and patient as known from traditional heterophoria measurement procedures albeit not by means of putting prism lenses in front of the patients' eyes but via the heads-up display adjustment.

In a last step, binocular balance testing will be achieved by binocular projection of targets for both eyes via heads-up displays. The binocular balance testing procedure will be performed in a similar interactive process between operator and patient as known from traditional binocular balance tests (e.g. red green test) albeit without the use of optical separators such as polarizing filters or red green filters but by individual monocular target projection under binocular target viewing conditions.

In an optional step, near vision testing can be performed by projection of virtual targets at various distances in front of the eye. The near vision testing procedure can be performed in a similar interactive process between operator and patient as known from traditional near vision tests albeit without the use of near addition lenses and real targets at close proximity to the eye but by projection of virtual targets at various distances in front of the eye.

Retinal image based objective refraction procedures can also be carried out using the apparatus depicted in FIG. 4.

Thereby, the wavefront aberrations, serving as input parameters for calculation of the final prescription, can be measured under binocular open space viewing conditions.

Figure 6:
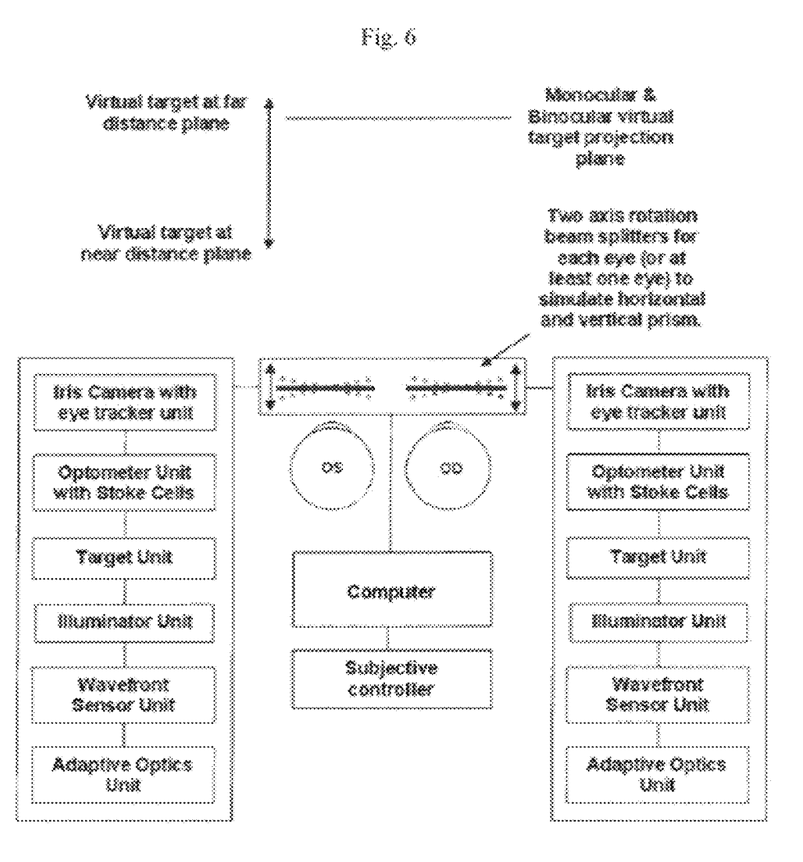
FIG. 6 schematically depicts another embodiment of a binocular vision analyzer apparatus.

FIG. 6 shows a table top design binocular heads-up refractor apparatus in accordance with an embodiment of the present invention that includes a wavefront sensor unit and an adaptive optics unit. The apparatus includes an adjustable binocular heads-up display of two virtual targets, a spherical correction device (e.g. a Badal Optometer) and a cylindrical correction device (e.g. a Stokes cell), a target unit, an illuminator unit, an iris camera, a wavefront sensor unit, an eye tracker unit and an adaptive optics unit.

The binocular heads-up refractor apparatus for combined objective and subjective refraction including adaptive optics depicted in FIG. 6 can include the following advantageous features:

a. A tabletop design;
b. Adjustable binocular heads-up display of two virtual targets, for control of vergence;
c. Ocular lower and higher-order aberration measurement;
d. The ability to automatically modify virtual, heads-up display of targets by compensating lower order or lower and higher order aberrations of the eye with the optometer and adaptive optics mirror as a start value for subjective refraction;
e. Open space monocular and binocular subjective refraction measurement;
f. Heterophoria measurement;
g. Binocular balance measurement;
h. The ability to employ retinal image based refraction techniques under binocular open space viewing conditions;
i. The ability to modify the virtual, heads-up display of targets by compensating/modifying higher-order aberrations of the eye based on the measurement of wavefront aberrations of the eye and compensations using an adaptive optics system; and
j. The ability to simulate the visual impact of optical designs such as single vision, multi focal, progressive designs of optical aids such as spectacles, contact lenses, IOLs, etc, by modifying lower and higher-order aberrations with the adaptive optics system and projecting those modified aberrations, corresponding to optical designs, via the heads-up display of targets into the eyes.

Figure 7:
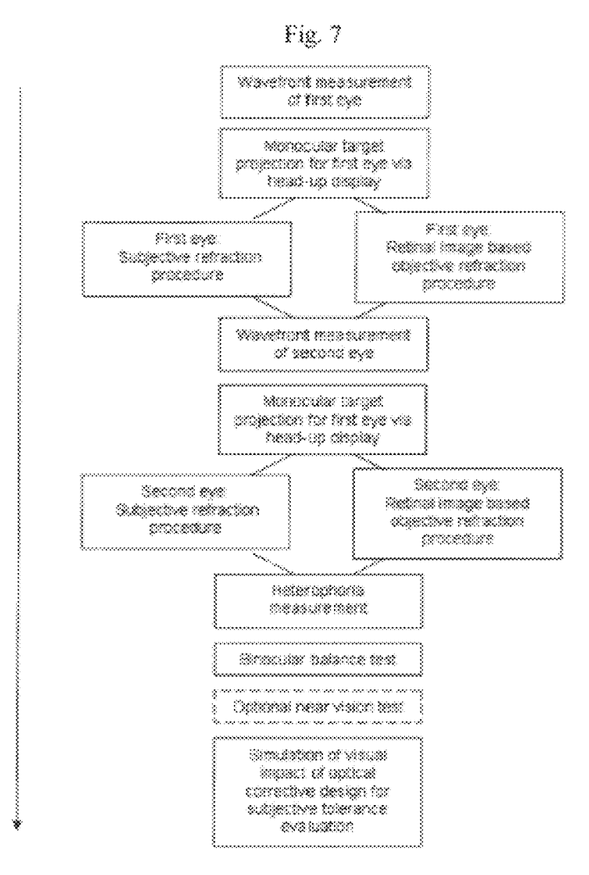
FIG. 7 shows a flow diagram of a method of using the analyzer apparatus of FIG. 6.

FIG. 7 shows various steps that can be carried out when using the apparatus depicted in FIG. 6. For the first eye, wavefront aberrations are measured objectively and lower order aberrations or lower and higher-order aberrations are compensated for via the optometer unit with Stokes cells in combination with the adaptive optics unit. Alignment of virtual target displays can be maintained by the eye tracking unit, which can monitor the positions of the eye and adjust the positions of the apparatus in response.

In a next step the subjective refraction procedure can be performed using the optometer unit with Stokes cells in a similar interactive process between operator and patient as known from traditional subjective refraction procedures albeit without physically positioning lenses in front of the patients' eyes but by modification of virtual target projection into the eye. Following monocular refraction of the first eye, the same process is repeated for the second eye.

Heterophoria measurement can be achieved by projection of state of the art heterophoria measurement tests (e.g. fixation disparity test) and via horizontal and/or vertical adjustment of beam splitters of the heads-up displays. The heterophoria measurement procedure can be performed in a similar interactive process between operator and patient as known from traditional heterophoria measurement procedures albeit not by means of putting prism lenses in front of the patients' eyes but via the heads-up display adjustment.

In a last step binocular balance testing can be achieved by binocular projection of targets for both eyes via heads-up displays. The binocular balance testing procedure can be performed in a similar interactive process between operator and patient as known from traditional binocular balance tests (e.g. red green test) albeit without the use of optical separators such as polarizing filters or red green filters but by individual monocular target projection under binocular target viewing conditions.

In an optional step, near vision testing can be performed by projection of virtual targets at various distances in front of the eye. The near vision testing procedure can be performed in a similar interactive process between operator and patient as known from traditional near vision tests albeit without the use of near addition lenses and real targets at close proximity to the eye but by projection of virtual targets at various distances in front of the eye.

Retinal image based objective refraction procedures can also be carried out using the apparatus depicted in FIG. 6.

Thereby, the wavefront aberrations, serving as input parameters for calculation of the final prescription, can be measured under binocular open space viewing conditions.

Additionally, optical designs for correcting the refractive error (e.g. spectacles. contact tenses or intraocular lenses) such as monofocal vision, progressive lens vision, or simultaneous vision multifocal lens designs can be simulated with the adaptive optics system. Thereby virtual targets representing the visual impact of optical correction methods can be projected into the eye and subjective patients' tolerance can be evaluated.

Figure 8:
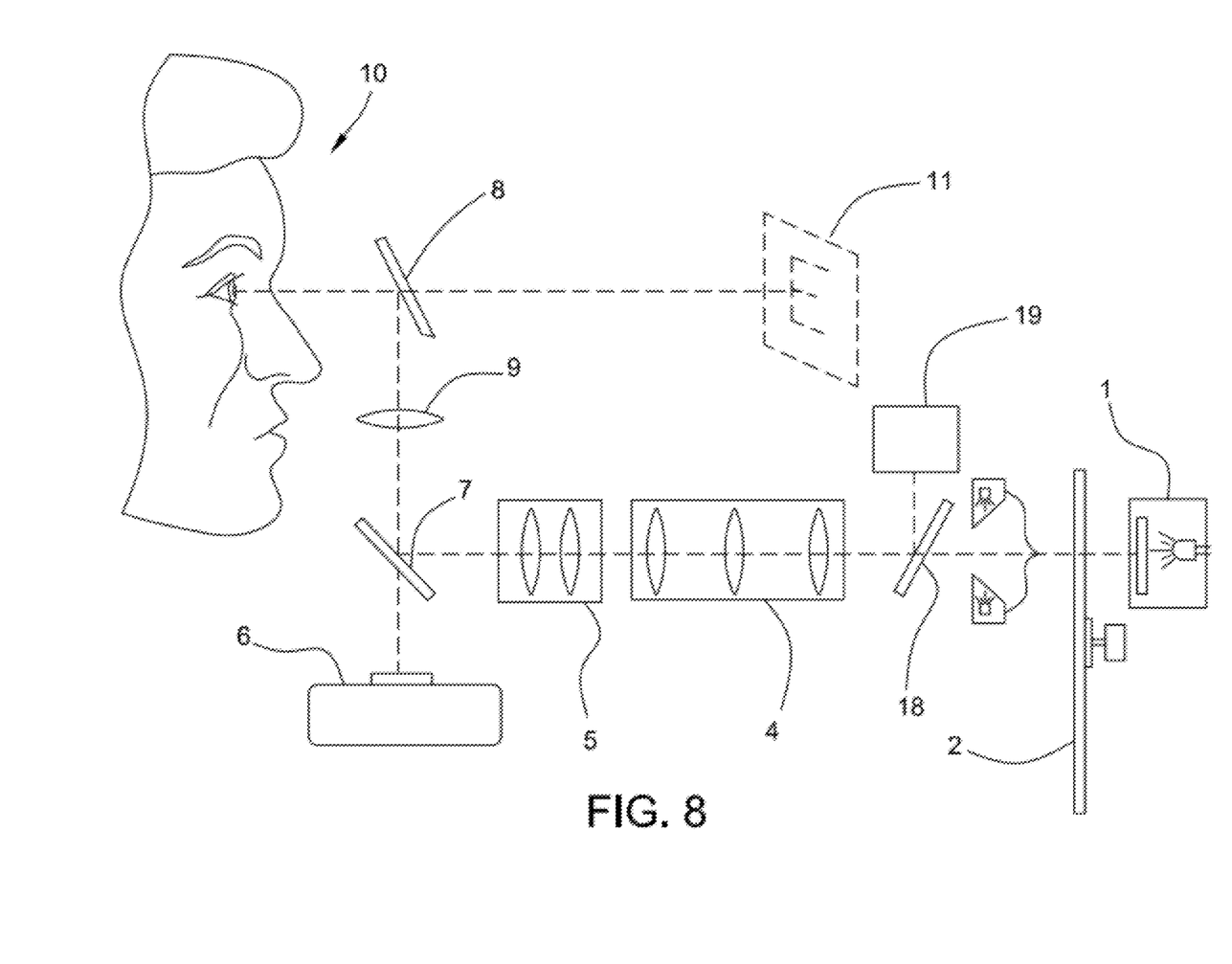
FIG. 8 shows a schematic illustrated view of components of an embodiment of a binocular vision analyzer apparatus corresponding to one eye.
Figure 9:
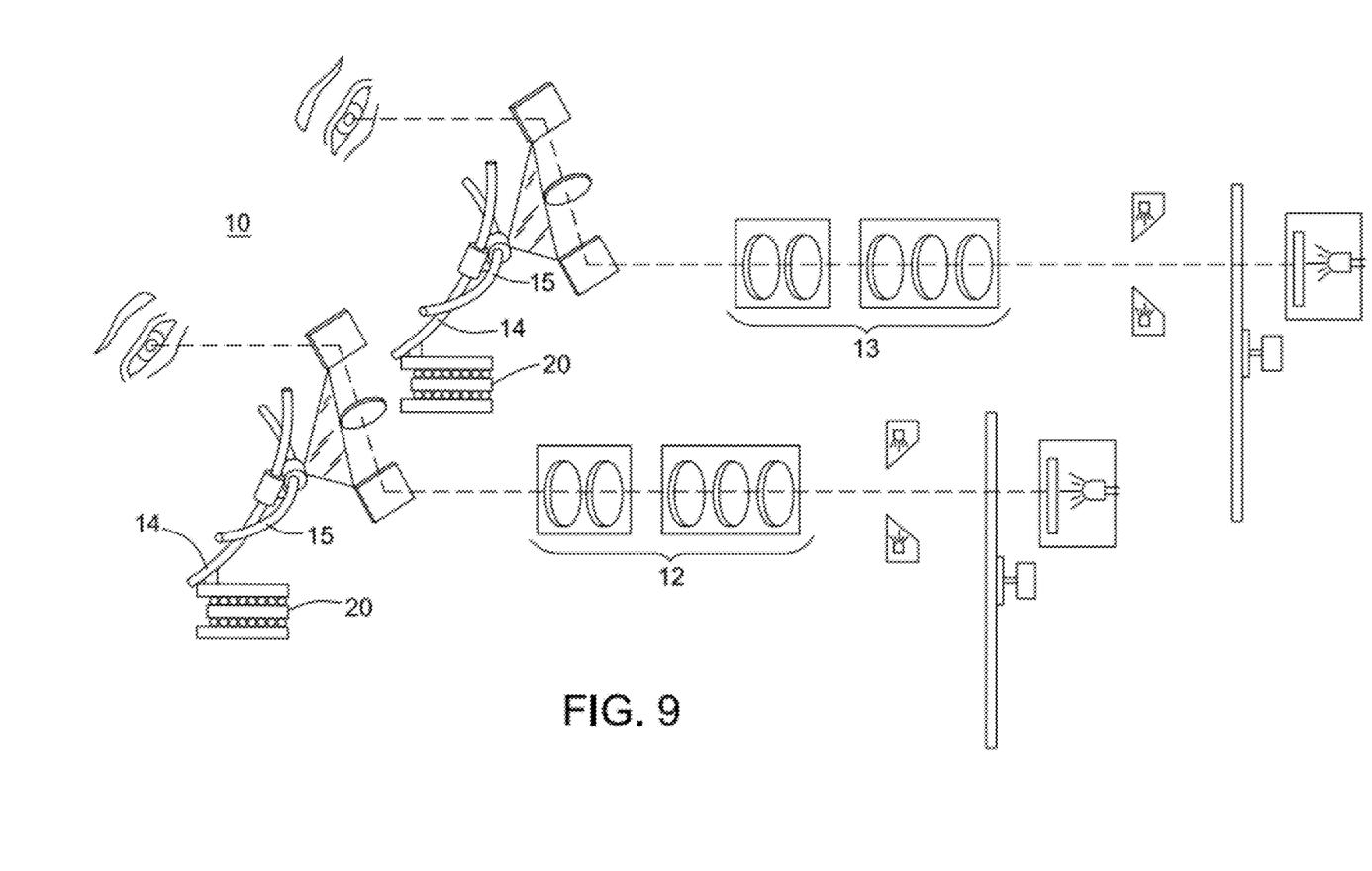
FIG. 9 shows a schematic illustrated view of select components of the apparatus of FIG. 8 corresponding to two eyes and including adjustment mechanisms.

Details of an exemplary embodiment of the binocular vision analyzer apparatus is shown in FIGS. 8 and 9. In this embodiment, an illumination module 1 projects light through a target 2 which is part of a target unit. The target unit could include one or more of a rotating wheel containing a plurality of targets, a linear strip containing a plurality of targets and a rectangle containing a plurality of targets. The illumination device may also be built into the target unit as in a miniature electronic screen (e.g., as used in mobile phone).

The light then passes through an optional glare module 3. This module provides a bright light or series of lights which are projected around the image of the target to create glare. If an individual 10 trying to discern a visual acuity target has a cataract in his eye he will be less able to discern the visual acuity target when the glare module is activated. Typically he will only be able to read a target with larger letters and the degree of increase in the size of the letters he can discern provides an indication of the degree of opacity of the cataract.

The light beam containing the target image is projected through a spherical correction device 4, which can be one of a Badal Optometer, a free-form lens (Alvarez or similar), a liquid lens or a holographic lens. The spherical correction device could also include a combination of these devices. In the embodiment shown in FIGS. 8 and 9 a single motor drives the central lens of a Badal optometer left and right in the diagram to achieve spherical correction. Motor steps are typically counted to provide a measure of the correction. The Badal optometer can allow a continuous variation of spherical correction which may be preferable for opticians and ophthalmologists compared to stepwise variations (e.g. created by replacing individual lenses) since the use of stepwise variations can cause the individual being tested to forget the effect of the previous image.

The light beam containing the target image then passes through a cylindrical correction device 5, which can be any one of a Stokes Cell, free-form lens (Alvarez or similar), liquid lens, holographic lens or a combination of these devices. In the embodiment that is depicted a pair of motors drive two cylinder lenses separately to achieve the required power and then together to achieve the required angle for cylindrical correction. Motor steps are typically counted to provide a measure of the correction. The use of a Stokes cell also allows a continuous variation of cylindrical correction, which again may be considered preferable by opticians and ophthalmologists, since stepwise variations (e.g. created by replacing individual lenses) can cause the individual being tested to forget the effect of the previous image.

An optical system is configured to direct an image of the target to the eye of a user. In the illustrated embodiment this system includes a beam-splitter 7 that directs the light beam containing the target image through a relay lens 9. The beam-splitter allows a beam impinging on the pupil camera 6 to be substantially collinear with the beam containing the target image. In the illustrated embodiment the beamsplitter 8 diverts the image of the eye downwards into the camera. This image can be used for tracking the motion of the eye. Beamsplitter 8 also projects the image of the target into the eye. The optics are designed to provide a virtual image 11 such that, to the individual, it appears that the image is floating in space. The spherical correction device can be adjusted to enable the image to appear to be at infinity, up close, or any position in between. When up close the effect is so powerful that the individual may put his hand out and try to grab the image of the projected target.

An optional beamsplitter 18 can be interposed in the beam path to enable a sensor unit 19 to measure sphere, and cylinder and angle. The sensor unit 19 can be an auto-refracting sensor unit or a wavefront sensor unit 18 that measures sphere, cylinder and angle, and higher order aberrations, which can be translated into corrections that can be applied by an adaptive optic device which typically could be used in place of individual spherical correction device 4 and cylindrical correction device 5 or could supplement these devices 4 and 5.

FIG. 9 depicts two sets of the optics shown in FIG. 8. One set of optics 12 is used for the right eye, and the other set 13 is used for the left eye. FIG. 9 also shows the structure that supports the optics. An X, Y, Z stage 20, commonly used in the art of metrology, is used as a positioning mechanism for each set of optics in order to supply the movements needed to correct for human variation of the position of an eye or to correct for eye motion. While the drawings only show one X, Y, Z stage, it may be understood that such a stage can be used with the optics corresponding to each eye. Attached to each stage 20 is an angular positioning mechanism for adjusting an angular position of the virtual target image with respect to the individual's eye. The angular positioning mechanism can include a first positioning goniometer 14 that allows nominally horizontal vergence motion about the eye. The goniometer 14 is, in turn, attached to a further positioning goniometer 15 allowing nominally vertical vergence motion about the eye. The center of the radius of the curved rails of goniomters 14 and 15, whether for horizontal vergence correction or vertical vergence correction, are nominally centered on the eye. In the illustrated embodiment the vertical vergence correction goniometer is attached to a structure that carries the optics for the corresponding eye.

All the motions in the embodiment can be manually moved or, in a preferred embodiment, moved by motors. Each motion in turn can be measured, either by a distinct measurement device as would be understood by those experienced in the art, or by means of motor encoder counts or stepper motor counts. In the case where encoder or motor counts are used it is advantageous to have a flag which operates a switch to provide an absolute position which can be used as a home position.

The computing device, or computer, described above with respect to the embodiment shown in FIG. 1, can store and retrieve data which can be used to adjust the optics for the right eye and the optics for the left eye in three nominally orthogonal axes. Further the data can be used to set at least one of the following: PD; spherical correction; cylinder correction; vergence settings; target settings and adaptive optics settings. This saves time when a patient returns since his or her settings can be repeated and only need minor refinement.

The targets projected can be any of the targets that those experienced in the art of optometric measurement are aware of, notably targets that are typically used monocularly: e.g. visual acuity, low contrast glare targets, special astigmatic test targets, red/green targets, targets to refine C+ and Cx measurements; or stereoscopically: e.g. Binocular balance, duo-chrome balance, fixation disparity, graded stereopsis, aniseikonia, random dot stereo, phoria, vergence and alignment.

To make the C+ and Cx targets easier to subjectively focus the cylindrical component can be enhanced in the relevant direction by adjusting the cylindrical correction device to apply increased cylinder in that direction For distance testing the virtual images appear as they are coming from infinity. To save space in an optometrist's or ophthalmologist's office it is very advantageous to remove the requirement for a lane and hence a screen can be placed close to the apparatus. In alternative embodiments the screen can be attached to a wall, mounted to the table upon which the apparatus is standing, or can be attached to the apparatus itself. The screen can be black felt, or other material which allows the images to stand out against the background of the screen. When using such a proximal screen, the image, if initially projected at infinity, will still appear at infinity. Preferably the screen is of sufficient size to overcome the potential problem of instrument myopia.

Most phoropters on the market today are devices wherein the nominal 20 ft. lane is realized as either a 20 foot lane, a 10 foot lane with a mirror at one end, or a shorter device with a series of folded mirrors which are bulky and tend to create instrument myopia. Phoropters typically require the operator to mix and match a significant number of lenses to providing the correct refraction or the lenses are in a bulky carousel that fences in the face of the individual, again causing instrument myopia. By comparison, the binocular vision analyzer apparatus described herein has nothing in front of the eyes except for a pair of beamsplitters which are no more invasive than spectacle lenses. To decrease any distraction, the beamsplitters can be partially frameless and provided with chamfers at each edge that are nominally aligned with a line struck from the pupil to the edge of the bevel, thus creating a chamfer that is less likely to be seen by the individual.

The apparatus, if miniaturized, can be realized as a head mounted apparatus or parts of the apparatus can be head mounted.

When projecting near targets, it may be beneficial to aid fusion by supplying a vergence assistance target that enables the individual to align his or her eyes at the appropriate depth of the virtual target. The vergence assistance target can be a tangible target, a tangible screen or a hologram. During use, the vergence assistance target is set at the correct distance to provide fused virtual images. The vergence assistance target can also utilize a plurality of targets disposed at various distances, or a target that is movable to set distances. For example, the vergence assistance target could be disposed on a rail in front of the patient's eyes and movable to different distances. Alternatively, a hologram with features at different distances could be used.

It may be beneficial to allow the patient to take control of a refractive variable. This can be achieved by providing a switch or control to the patient so that he can control selected variables, e.g. sphere and cylinder, corresponding to at least one of the spherical correction device, cylindrical correction device and adaptive optics.

The computing device can also store data from one of a separate vision analyzer, auto-refractor, wavefront refractor and lens analyzer. This can be useful for obtaining start values which can be applied through motorization or manual means to the spherical correction device and cylindrical correction device, and in the case of the wavefront refractor, can also be applied to an adaptive optic to correct for higher-order aberrations.

The computing device can also be used to store, in the memory or in an external data base, the refraction values from at least one of present, previous and alternative refractions. Through motorization or manual means these corrections can be projected to the individual for comparative purposes.

In some cases it may be advantageous for the individual to wear his glasses during a refraction. The reason for this is that the individual being tested may habitually wear his glasses at an angle or too low or high relative to the eyes. In stronger prescriptions this can induce significant errors. By over-refracting, the instrument is measuring the difference between his old prescription and the new refraction—and in this case most of the errors induced by the habitual position of the spectacles are cancelled. The binocular vision analyzer beamsplitters can be sufficiently distant from the eyes to enable glasses to be worn. This gives the binocular vision analyzer a significant advantage over most other phoropter devices where there are, in nearly all cases, lenses at the spectacle plane.

While the invention has been particularly shown and described with reference to preferred embodiments thereof, it will be understood by those skilled in the art that various changes in form and details may be made therein without departing from the spirit and scope of the invention.

What is claimed is:

1. A method for determining a prescription of visual aids for first and second eyes of an individual, the method comprising:
    providing first and second targets respectively corresponding to the first and second eyes of the individual;
    illuminating the first and second targets using at least one illumination device;
    disposing a first beam splitter in front of the first eye so as to reflect visible light from the first target into the first eye and to transmit visible light from space behind the beam splitter into the first eye so that a virtual image of the first target appears to the individual as a heads-up display floating in the space behind the beam splitter in a line of sight of the first eye;
    disposing a second beam splitter in front of the second eye so as to reflect visible light from the second target into the second eye and to transmit visible light from space behind the beam splitter into the first eye so that a virtual image of the second target appears to the individual as a heads-up display floating in the space behind the beam splitter in a line of sight of the second eye;
    selecting a spherical correction for each of the first and second eyes using respective first and second spherical correction devices;
    selecting a cylindrical correction for each of the first and second eyes using respective first and second cylindrical correction devices; and
    determining the prescription of visual aids for the first and second eyes based respectively on the selected spherical correction and cylindrical correction for the first and second eyes.

2. The method recited in claim 1, further comprising monitoring a position and movement of at least the first eye using at least one position monitoring device.

3. The method recited in claim 2, wherein the position monitoring device includes a camera focused on a portion of at least the first eye.

4. The method recited in claim 2, further comprising positioning at least one of the individual's head and components of the apparatus using a positioning device so as to accommodate monitored changes in a position of at least the first eye.

5. The method recited in claim 4, further providing a measurement of the pupillary distance based on a required change in position performed by the positioning mechanism to align the pupil of at least one eye.

6. The method recited in claim 1, wherein the first and second spherical correction devices each include at least one of a Badal optometer, a free-form lens, a liquid lens and a holographic lens.

7. The method recited in claim 1, wherein at least one of the spherical correction device and cylindrical correction device is configured to provide continuous dioptric correction.

8. The method recited in claim 1, wherein each of the first and second cylindrical correction devices includes at least one of a Stokes Cell, a free form lens, a liquid lens and a holographic lens.

9. The method recited in claim 1, further comprising disposing first and second glare modules in front of the first and second targets so as to provide light around the respective targets.

10. The method recited in claim 1, further comprising moving components of the optical system using an angular positioning mechanism so as to provide angular movement of the first virtual image about horizontal and vertical axes with respect to the second virtual image so as to provide horizontal and vertical vergence control.

11. The method recited in claim 10, wherein the angular positioning mechanism providing movement of the first virtual image about horizontal and vertical axes with respect to the second virtual image includes at least one of a positioning goniometer and a pivot.

12. The method recited in claim 4, further comprising providing at least one adaptive optics unit so as to simulate a vision correction aid for subjective feedback.

13. The method recited in claim 1, further comprising storing, in a computing device including a memory, patient settings of at least one variable corresponding to at least one of the first and second eyes from the list of: eye position in three axes, pupillary distance, spherical correction, cylinder correction, vergence setting, target setting, target brightness and adaptive optics setting.

14. The method recited in claim 1, further comprising presenting third and fourth targets respectively corresponding to the first and second eyes, wherein each of the first and third targets and second and fourth targets form a pair of targets configured to measure cylindrical correction of the respective eye, the respective targets in each pair being disposed at 45 degrees to each other and configured for measuring C+ and Cx values as a basis for calculating cylinder and axis.

15. The method recited in claim 14, further comprising supplying supplemental cylinder in a direction of the C+ and Cx targets so as to aid the individual in target focusing.

16. The method recited in claim 1, further comprising measuring sphere and cylinder corresponding to each of the first and second eyes using respective first and second sensor units, the first and second sensor units each comprising at least one of a wavefront sensor unit and an auto-refractor sensor unit, each of the first and second sensor units being disposed opposite the respective spherical and cylindrical correction devices with respect to the respective first and second eyes such that light from the respective eyes entering the respective sensor unit has passed through at least one of the respective spherical and cylindrical correction devices.

17. The method recited in claim 1, further comprising providing a vergence assistance target for assisting the individual with fusing the first and second virtual images for near testing.

18. The method recited in claim 16, wherein the vergence assistance target includes at least one of a hologram and a measuring rail configured to provide a target at variable distances.

19. The method recited in claim 17, wherein the hologram includes features disposed at different distances.

20. The method recited in claim 1, further comprising providing a control to the individual and directing the individual to adjust at least one of the spherical correction device, cylindrical correction device and vergence correcting device using the control.

21. The method recited in claim 1, further comprising providing the apparatus with a computing device and receiving data imported from at least one of a separate vision analyzer, auto-refractor, wavefront refractor and lens analyzer.

22. The method recited in claim 1, further comprising storing refraction values from at least one of a present, previous and alternative refraction in a data base, and presenting the stored refraction values to the individual for a comparison.

23. The method recited in claim 1, further comprising directing the individual to wear spectacles during the method.

24. The method recited in claim 1, wherein the first beam splitter and second beam splitter each include a chamfer having an angle configured to be substantially aligned with a line extending radially outward from the first and second eyes, respectively.

25. The method recited in claim 1, wherein each of the first and second targets are disposed in respective first and second target units.

26. The method recited in claim 25, wherein each target unit includes a plurality of additional targets, and each target unit includes one of a rotating wheel of targets, a linear strip of targets, and a rectangle of targets.

27. The method recited in claim 1, further comprising providing a screen which is visible to the first and second eyes together with the first and second virtual image.

28. The method recited in claim 25, wherein the first and second target units and at least one illumination device comprise an electronic screen.

29. The method recited in claim 1, wherein there is nothing disposed between the first eye and the first beam splitter and wherein there is nothing disposed between the second eye and the second beamsplitter.

* * * * *